United States Patent
Ebisawa

(10) Patent No.: US 9,329,683 B2
(45) Date of Patent: May 3, 2016

(54) METHOD FOR DETECTING POINT OF GAZE AND DEVICE FOR DETECTING POINT OF GAZE

(75) Inventor: Yoshinobu Ebisawa, Hamamatsu (JP)

(73) Assignee: NATIONAL UNIVERSITY CORPORATION SHIZUOKA UNIVERSITY (JP)

( * ) Notice: Subject to any disclaimer, the term of this patent is extended or adjusted under 35 U.S.C. 154(b) by 366 days.

(21) Appl. No.: 13/992,877

(22) PCT Filed: Dec. 7, 2011

(86) PCT No.: PCT/JP2011/078302
§ 371 (c)(1),
(2), (4) Date: Aug. 26, 2013

(87) PCT Pub. No.: WO2012/077713
PCT Pub. Date: Jun. 14, 2012

(65) Prior Publication Data
US 2013/0329957 A1    Dec. 12, 2013

(30) Foreign Application Priority Data
Dec. 8, 2010 (JP) .................. 2010-274074

(51) Int. Cl.
*A61B 3/113* (2006.01)
*G06K 9/00* (2006.01)
(Continued)

(52) U.S. Cl.
CPC ............... *G06F 3/013* (2013.01); *A61B 3/113* (2013.01); *G02B 27/0093* (2013.01); *G06K 9/00604* (2013.01)

(58) Field of Classification Search
CPC .... A61B 3/113; G06K 9/00604; G06F 3/013; G06T 2207/30041
See application file for complete search history.

(56) References Cited

U.S. PATENT DOCUMENTS

| 6,578,962 B1 * | 6/2003 | Amir et al. ..................... 351/209 |
| 6,659,611 B2 * | 12/2003 | Amir et al. ..................... 351/210 |
| 7,533,988 B2 * | 5/2009 | Ebisawa ......................... 351/206 |

(Continued)

FOREIGN PATENT DOCUMENTS

| JP | 2005-185431 | 7/2005 |
| JP | 2005-198743 | 7/2005 |

(Continued)

OTHER PUBLICATIONS

Chen et al., "3D Gaze Estimation with a Single Camera without IR Illumination", Pattern Recognition, 2008. ICPR 2008. 19th International Conference on, 1-4.*

(Continued)

*Primary Examiner* — Katrina Fujita
(74) *Attorney, Agent, or Firm* — Ostrolenk Faber LLP

(57) ABSTRACT

A gaze point detection device 1 has four cameras 2a, 2b, 2c, 2d, light sources 3a, 3b, 3c, 3d, control circuits 4, 5, 6, and an image processor 7. The image processor 7 calculates vectors r, each of which is from a corneal reflection point to the center of a pupil, on a plane that is vertical to base lines. The image processor 7 also calculates angles θ of the line of sight on the basis of the vectors r and by using a function f including M parameters. Moreover, the image processor 7 determines the M parameters based on the angles θ, and detects a point of gaze Q based on the line of sight direction calculated using the determined parameters. The number of cameras is set at M×½ or higher.

4 Claims, 12 Drawing Sheets

(51) Int. Cl.
*G06F 3/01* (2006.01)
*G02B 27/00* (2006.01)

(56) References Cited

U.S. PATENT DOCUMENTS

| | | | | |
|---|---|---|---|---|
| 7,533,989 | B2* | 5/2009 | Ebisawa | 351/208 |
| 7,686,451 | B2* | 3/2010 | Cleveland | 351/210 |
| 7,766,479 | B2* | 8/2010 | Ebisawa | 351/209 |
| 7,809,160 | B2* | 10/2010 | Vertegaal et al. | 382/103 |
| 7,963,652 | B2* | 6/2011 | Vertegaal et al. | 351/205 |
| 2007/0014552 | A1* | 1/2007 | Ebisawa | 396/51 |
| 2007/0279590 | A1* | 12/2007 | Ebisawa | 351/208 |
| 2009/0219484 | A1* | 9/2009 | Ebisawa | 351/210 |
| 2011/0242486 | A1* | 10/2011 | Ebisawa | 351/206 |

FOREIGN PATENT DOCUMENTS

| | | |
|---|---|---|
| JP | 2005-230049 | 9/2005 |
| JP | 2008-029702 | 2/2008 |
| JP | 2009-297323 | 12/2009 |
| WO | WO 2007/113975 | 10/2007 |

OTHER PUBLICATIONS

Ebisawa "Robust pupil detection by image difference with positional compensation" Virtual Environments, Human-Computer Interfaces and Measurements Systems, 2009. VECIMS '09. IEEE International Conference on, 143-148.*

Kang et al., "Investigation of the Cross-Ratios Method for Point-of-Gaze Estimation", 2008, Biomedical Engineering, IEEE Transactions on, vol. 55, Iss: 9, 2293-2302.*

Ohno et al., "A Free-head, Simple Calibration, Gaze Tracking System That Enables Gaze-Based Interaction", Proceedings of the 2004 symposium on Eye tracking research & applications, 115-122.*

Pylvänäinen et al. "Gaze tracking for near to eye displays." Proceedings of the 18th international conference on artificial reality and telexistence (ICAT 2008), 5-11.*

Villanueva et al., "A Novel Gaze Estimation System With One Calibration Point", 2008, Systems, Man, and Cybernetics, Part B: Cybernetics, IEEE Transactions on, vol. 38, Iss: 4, 1123-1138.*

Kondo et al. "3D Eye-Gaze Detection System Using Stereo-Calibrated Cameras", Proceeding of Vision Engineering Workshop 2009 (ViEW 2009), Dec. 3, 2009, 343-348.*

Kondou et al., "Easy Eye-Gaze Calibration using a Moving Visual Target in the Head-Free Remote Eye-Gaze Detection System", Virtual Environments, Human-Computer Interfaces and Measurement Systems, 2008. VECIMS 2008. IEEE Conference on, 145-150.*

International Search Report mailed Mar. 13, 2012 in corresponding PCT International Application No. PCT/JP2011/078302.

Elias Daniel Guestrin et al. "General Theory of Remote Gaze Estimation Using the Pupil Center and Corneal Reflections," IEEE Transactions on Biomedical Engineering, vol. 53, No. 6, Jun. 2006, pp. 1124-1133.

International Preliminary Report on Patentability mailed Jun. 20, 2013 issued in corresponding International Application No. PCT/JP2011/078302.

* cited by examiner (a)  (b)

US 9,329,683 B2

METHOD FOR DETECTING POINT OF GAZE AND DEVICE FOR DETECTING POINT OF GAZE

CROSS-REFERENCE TO RELATED APPLICATIONS

The present application is a 35 U.S.C. §§371 national phase conversion of PCT/JP2011/078302, filed Dec. 7, 2011, which claims priority to Japanese Patent Application No. 2010-274074, filed Dec. 8, 2010, the contents of which are incorporated herein by reference. The PCT International Application was published in the Japanese language.

TECHNICAL FIELD

The present invention relates to a gaze point detection method and a gaze point detection device for detecting a point of gaze of a subject on a predetermined plane on the basis of an image of the subject.

BACKGROUND ART

A device for detecting a line of sight or a point of gaze of a test subject in a non-contact manner has been considered important in the field of human interaction. If the high-precision line of sight detection technology is put to practical use, such device can be applied to various applications such as monitoring a driver, studying the level of interest in a certain product, and inputting data to a personal computer of a severely disabled person.

According to the line of sight detection methods disclosed in Patent Literature 1 and 2, a test subject is caused to gaze at a camera located in a known position and one point on a display screen located in a known position, and a function for calculating a line of sight direction of the test subject from the distance between the center of a pupil and a corneal reflection point is corrected, to detect the line of sight direction using the corrected function. These line of sight detection methods are capable of precisely detecting a line of sight, even when the test subject moves his/her head. The gaze detection method disclosed in Patent Literature 3 is a method for simultaneously detecting lines of sight of both eyes by using two cameras. According to this method as well, the test subject is required to look at the cameras in order to calibrate the results of detecting the lines of sight.

The reason that the test subject is required to look at the cameras in order to execute correction upon line of sight calculation is because a corneal reflection image of a light source is actually shifted from the center of each pupil although the corneal reflection image is ideally located in the center of each pupil due to the symmetry with respect to the optical axis of each eyeball. For this reason, when using the function to calculate the line of sight direction of the test subject from the distance |r|, the gain value included in the function cannot be accurately obtained unless so-called origin correction is executed. Each of the conventional technologies mentioned above, therefore, corrects the function by causing the test subject to gaze at a specified point including the position of the camera.

CITATION LIST

Patent Literature

Patent Literature 1: Japanese Patent Application Publication No. 2005-185431

Patent Literature 2: Japanese Patent Application Publication No. 2005-230049

Patent Literature 3: Japanese Patent Application Publication No. 2005-198743

Causing the test subject to gaze at a camera means that the test subject is required to gaze at the center of the aperture of the camera (the center of the lens), which makes it difficult to determine the viewpoint of the test subject because the object to be gazed at is ambiguous. Although the viewpoint of the test subject could be determined easily by attaching an obvious target (a marker) to the center of the lens, it becomes difficult to accurately detect the line of sight of the test subject because the target appears on a camera image as an obstacle. In a case where the camera is installed on the lower side of the front side of the test subject for securing an installation site and the test subject is caused to look at the camera, the pupils of the test subject become small due to near reflexes thereof. Moreover, the test subject has corneal reflexes overlapping with it, which makes it difficult to accurately detect the positions of the pupils from the camera image. The error on the distance |r| that is calculated when the test subject looks at the camera has a strong effect on a gain value obtained as a result of calibration, and causes a great error on the viewpoint of the test subject or a line of sight detection result over the entire display screen.

It is generally expected that calibration accuracy in line of sight detection can be improved to some extent by displaying a number of targets sequentially on the screen and causing the test subject to look at the targets, the positions of the targets being known. Unfortunately, it is inevitable that such a calibration process takes a lot of time, and the longer the calibration time, the greater the burden on the test subject, resulting in a decrease of concentration of the test subject and calibration accuracy. The line of sight detection method of Patent Literature 3 also realizes calibration of tracing two points having known coordinates on the display or calibration in which a moving point (a one which position is known at a certain time) is traced. However, this calibration method requires the test subject to look at two or more specific targets. In addition, there is caused an error in a relative position between a corneal reflection of each pupil and the center of each pupil looking at the center of the aperture of the camera. Consequently, calibration does not help obtain the gain value accurately. Therefore, although errors occur at the point of gaze on the display screen on a regular basis, changes in the value of errors resulting from the positions of the gaze make it difficult to correct such errors.

SUMMARY OF INVENTION

Technical Problem

The present invention was contrived in view of such problems, and an object thereof is to provide a gaze point detection method and a gaze point detection device capable of realizing high-speed and highly accurate gaze point detection while reducing the burden on a test subject.

Solution to Problem

To solve the object described above, a gaze point detection method according to one aspect of the present invention has: a face image generation step of generating face images of a subject by using an number of N cameras (N is a natural number of 2 or more) and a plurality of light sources; a vector calculation step of calculating vectors r based on the face images generated by the N number of cameras, the vectors r each representing an actual distance between a center of a pupil of the subject and a corneal reflection point on a cornea of the subject on which light from the light sources reflects; a line of sight direction calculation step of calculating angles θ of a gaze of the subject with respect to base lines connecting the center of the pupil and the N number of cameras, based on the vectors r corresponding to the N number of cameras, by using the following formula (1) in use of a function f and an M number of undetermined constants (M is a natural number of 3 or more) including at least an offset vector $r_0$ of each of the vectors r;

$$\theta = f(|r - r_0|) \quad (1)$$

an undetermined constant determination step of determining the M number of undetermined constants included in the function f, by using a plurality of relational expressions that are derived based at least on the angles θ calculated with respect to the N number of cameras; and a gaze point detection step of detecting a point of gaze of the subject on the basis of the line of sight direction calculated in the line of sight direction calculation step, by using the M number of undetermined constants determined in the undetermined constant determination step, wherein the number N of cameras is set at M×½ or higher.

A gaze point detection device according to one aspect of the present invention is a device for detecting a point of gaze of a subject based on face images of the subject, this device having: an N number of cameras for acquiring the face images of the subject; a plurality of light sources; a control circuit for controlling the cameras and the light sources; and an image processing unit for processing image signals output from the N number of cameras, wherein the image processing unit: calculates vectors r based on the face images generated by the N number of cameras, the vectors r each representing an actual distance between a center of a pupil of the subject and a corneal reflection point on a cornea of the subject on which light from the light sources reflects; calculates angles θ of a line of sight of the subject with respect to base lines connecting the center of the pupil and the N number of cameras, based on the vectors r corresponding to the N number of cameras, by using the following formula (1) in use of a function f and M number of undetermined constants (M is a natural number of 3 or more) including at least an offset vector $r_0$ of each of the vectors r;

$$\theta = f(|r - r_0|) \quad (1)$$

determines the M number of undetermined constants included in the function f, by using a plurality of relational expressions that are derived based at least on the angles θ calculated with respect to the N number of cameras; detects a point of gaze of the subject on the basis of the line of sight direction calculated using the formula (1) by using the M number of undetermined constants; and sets the number N of cameras at M×½ or higher.

The gaze point detection method or gaze point detection device described above generates the face images of the subject by means of the N number of cameras and the plurality of light sources, calculates the vectors r with respect to the N number of cameras based on the face images, the vectors r each from the corneal reflection point of the subject to the center of the pupil of the subject, and calculates the angles θ of the line of sight with respect to the base lines for the gaze of the subject, corresponding to the N number of cameras, by applying the vectors r to the function f that includes the M number of undetermined constants including the offset vectors $r_0$. The method or device also derives a plurality of relational expressions based on the angles θ calculated as described above, sets the number of cameras at M×½ or higher, and thereby determines the M number of undetermined constants of the function f by using these relational expressions. By using the determined function f, the line of sight direction and the point of gaze are detected from the face images of the subject. In this manner, automatic correction on the function for calculating the line of sight direction can be executed with a high degree of accuracy, without requiring the subject to gaze at a plurality of specified points or the apertures of the cameras. Consequently, the burden on the subject can be reduced, and high-speed and highly accurate gaze point detection can be performed.

Advantageous Effects of Invention

The gaze point detection method and gaze point detection device according to the present invention can realize high-speed and highly accurate gaze point detection while reducing the burden imposed on a test subject.

DESCRIPTION OF EMBODIMENTS

Figure 1:
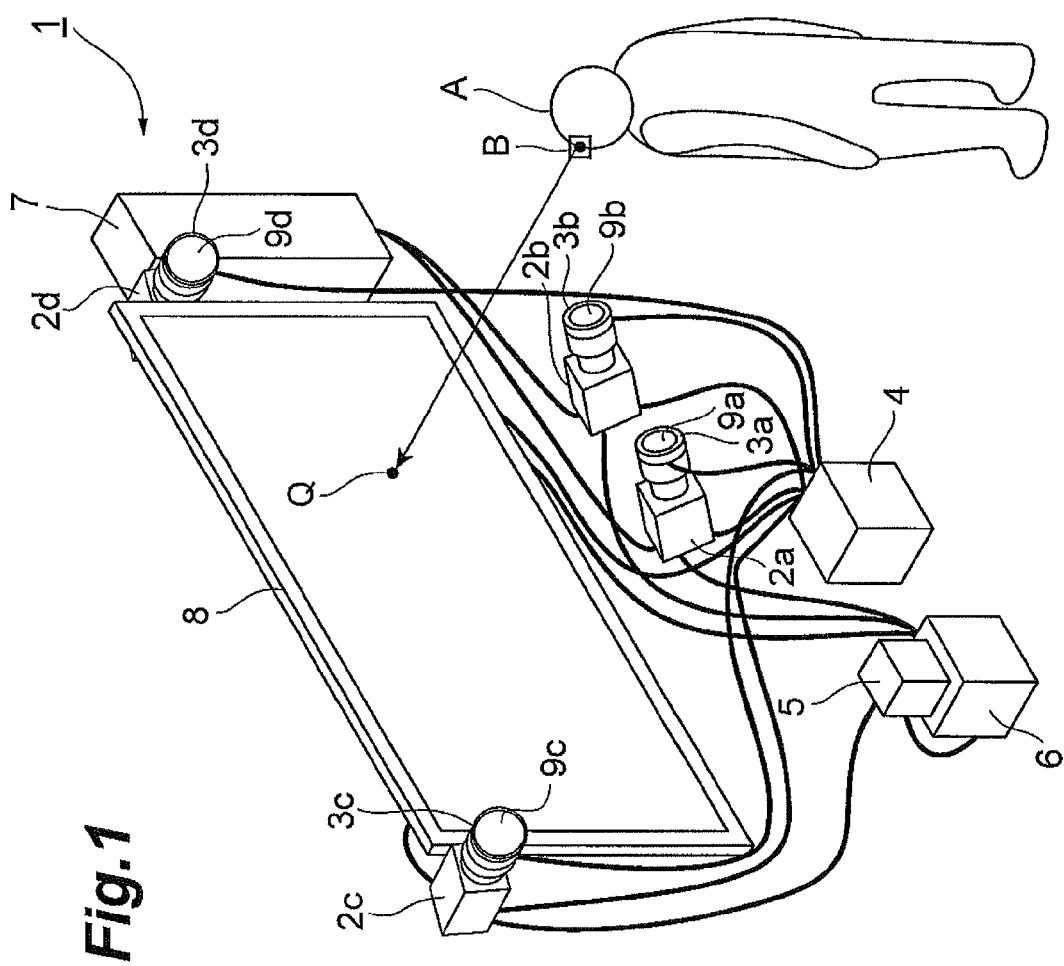
FIG. 1 is a perspective view showing a gaze point detection device 1 according to a preferred embodiment of the present invention.

A preferred embodiment of a gaze point detection method and a gaze point detection device according to the present invention is described hereinafter in detail with reference to the drawings. Note in the following descriptions of the drawings that like reference numerals are used to indicate the same or like portions in each of the diagrams, and the overlapping descriptions are omitted.

(Configuration of the Device for Detecting a Point of Gaze)

First, a configuration of a gaze point detection device for implementing the gaze point detection device of the present invention is now described with reference to the drawings. The device for detecting a point of gaze ("gaze point detection device," hereinafter) is a device for detecting a gaze point on a monitor screen of an information processing terminal, such as a personal computer, based on a face image of a subject.

FIG. 1 is a perspective view showing a gaze point detection device 1 according to a preferred embodiment of the present invention. As shown in the diagram, the gaze point detection device 1 has four cameras 2a, 2b, 2c, 2d for capturing face images of a subject A, light sources 3a, 3b, 3c, 3d provided outside imaging lenses of apertures of the cameras 2a, 2b, 2c, 2d, respectively, a light-emitting circuit (control circuit) 4 for feeding power to the light sources 3a, 3b, 3c, 3d, a synchronizing signal generator (control circuit) 5 for generating synchronizing signals to be input to the cameras 2a, 2b 2c, 2d, a delay circuit (control circuit) 6 for delaying the synchronizing signals, an image processor (image processing unit) 7, such as a personal computer, for processing image signals generated by the cameras 2a, 2b, 2c, 2d, and a display device 8 that is disposed above the cameras 2a, 2b and between the cameras 2c, 2d in such a manner as to face the subject A and connected to the image processor 7. The light-emitting circuit 4, the synchronizing signal generator 5 and the delay circuit 6 are control circuits for controlling the operations of the cameras 2a, 2b, 2c, 2d and of the light sources 3a, 3b, 3c, 3d.

The cameras 2a, 2b, 2c, 2d generate image data by capturing images of the face of the subject A. Cameras of NTSC system, a type of an interlaced scanning system, are used as the cameras 2a, 2b, 2c, 2d. With the NTSC system, 30 frames of image data obtained per second are each composed of an odd field which is constituted by odd horizontal pixel lines and an even field which is constituted by even horizontal pixel lines except for the odd field. The image of the odd field and the image of the even field are captured and generated alternately at intervals of 1/60 of a second. Specifically, within one frame, the pixel lines of the odd field and the pixel lines of the even field are generated alternately to be side-by-side.

The cameras 2a, 2c, 2d receive input of delayed vertical synchronizing signals (VD signals) from the synchronizing signal generator 5 via the delay circuit 6, so that the four cameras 2a, 2b, 2c, 2d capture images at different times.

Figure 2:
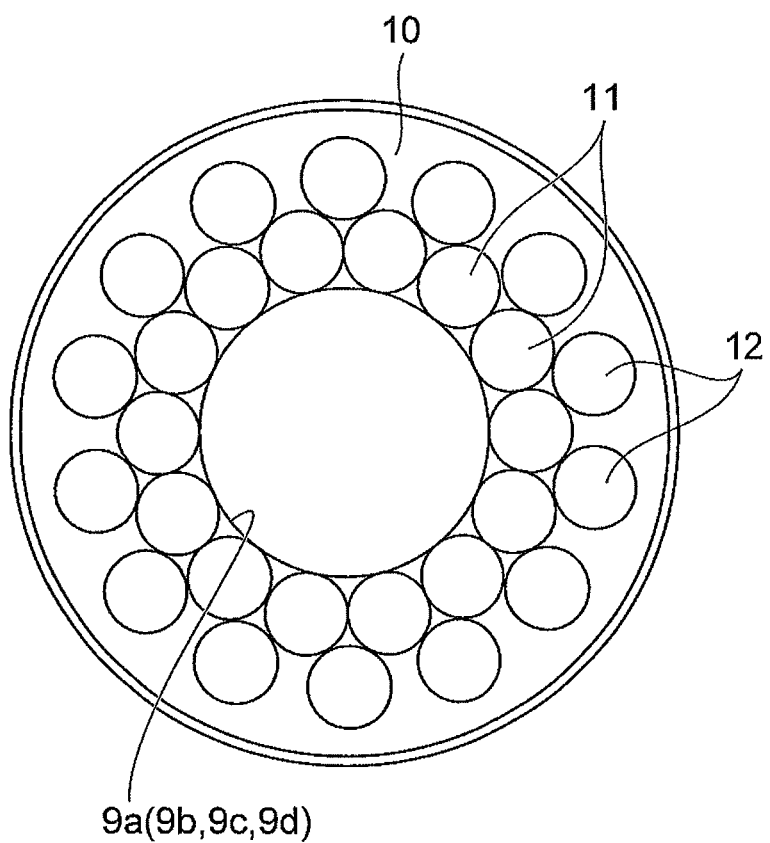
FIG. 2 is a plan view of a light source mounted on an aperture of a camera shown in FIG. 1.

The light sources 3a, 3b, 3c, 3d are fixed on the outside of the circular apertures 9a, 9b, 9c, 9d accommodating objective lenses of the cameras 2a, 2b, 2c, 2d. FIG. 2 shows a plan view of one of the light sources 3a, 3b, 3c, 3d. The light sources 3a, 3b, 3c, 3d radiate illumination light toward the face of the subject A, and has a plurality of two types of light-emitting elements 11, 12 embedded in a ring-shaped base part 10. The light-emitting elements 11 are semiconductor light-emitting elements (LED) with a center wavelength of 850 nm at their output light, and arranged into a ring at regular intervals along the rim of each of the apertures 9a, 9b, 9c, 9d on the base part 10. The light-emitting elements 12 are semiconductor light-emitting elements with a center wavelength of 950 nm at their output light, and arranged on the outside of the light-emitting elements 11 on the base part 10 into a ring at regular intervals. In other words, the distance between each light-emitting element 12 and the optical axis of each of the cameras 2a, 2b, 2c, 2d is greater than the distance between each light-emitting element 11 and the optical axis of each camera. Here, each of the light-emitting elements 11, 12 is provided on the base part 10 in such a manner as to emit the illumination light along the optical axis of each of the cameras 2a, 2b, 2c, 2d. Note that the configuration of the light sources is not limited the one described above, and therefore other configurations can be employed as long as the cameras are considered as the pinhole camera model.

The light-emitting circuit 4 is capable of controlling emission timings of the light-emitting elements 11, 12 independently. Specifically, in accordance with the shutter timings of the cameras 2a, 2b, 2c, 2d that are synchronized with the \TD signals from the synchronizing signal generator 5, the light-emitting circuit 4 controls the emission timings such that the light-emitting elements 11, 12 emit light alternately.

Such an operation of the control circuit generates a bright pupil image of left and right eyeballs B of the subject A when the illumination light is radiated from the light-emitting elements 11 to the eyeballs B, and a dark pupil image of the eyeballs B when the illumination light is radiated from the light-emitting elements 12 to the eyeballs B. The reasons are as follows: compared to the illumination light having a wavelength longer than 900 nm, the illumination light with a wavelength shorter than 900 nm makes the pupils brighter, but the pupils appear to be darker when the illumination light enters the eyeballs B from a position away from the optical axis of each camera. Four of the light-emitting elements 11 and four of the light-emitting elements 12 are lit alternately in such a manner as to be synchronized with the imaging timings for the cameras 2a, 2b, 2c, 2d to obtain the odd field and even field. As a result, the bright pupil image and the dark pupil image of the eyeballs B are reflected in the odd field and the even field generated by the cameras 2a, 2b, 2c, 2d.

The image processor 7 processes image data output from the four cameras 2a, 2b, 2c, 2d. Specifically, the image processor 7 separates one frame of image data output from the cameras 2a, 2b, 2c, 2d into an odd field and an even field. For example, the image data in the odd field (odd image data) corresponds to the bright pupil image, and the image data in the even field (even image data) corresponds to the dark pupil image. These image data have the valid pixels only in the odd field or the even field. Thus, the image processor 7 generates the bright pupil image data and the dark pupil image data by incorporating the average brightness of the pixel lines of the adjacent valid pixels into a pixel value between the lines.

The image processor 7 also repeatedly detects the left and right pupils of the subject A using the bright pupil image data and the dark pupil image data. In other words, the image processor 7 generates a difference image between the bright pupil image data and the dark pupil image data, sets a window based on the position of the pupils detected in the previous pupil detection process, and searches for the pupils in this window. More specifically, the image processor 7 binarizes the difference image by a threshold value determined by a percentile method, executes isolated point removal and labeling, and then selects, from labeled pixel connection components, pupil candidates from shape parameters such as the area, size, area ratio, squareness, and pupil feature value which are likely to represent the characteristics of the pupils. Out of the connection components of the selected pupil candidates, the image processor 7 determines two pupil candidates in a certain relationship as the left and right pupils, and calculates the central coordinates of the left and right pupils according to the image data.

Based on the bright pupil image data and the dark pupil image data, the image processor 7 also detects the position of a corneal reflection point on the cornea of each of the left and right eyes of the subject A where light from the light sources reflects. In other words, the image processor 7 sets a window having each detected pupil in the middle, creates image data, the resolution of which is increased only in this window, and detects the corneal reflection from the image data. Specifically, the image processor 7 determines a binarization threshold by means of the percentile method, creates a binarized image from this image, executes labeling, and selects a part whose area is equal to or less than a certain value. In so doing, the image processor 7 applies a separability filter to the central coordinates of the selected part, obtains a feature value by multiplying the degree of separability by the brightness, and determines that the corneal reflection is not detected when the feature value is equal or less than a certain value. In relation to the each of bright and dark pupil image data, the image processor 7 also calculates the distance in which the corneal reflection moves, and takes this distance as a differential position correction amount. The image processor 7 then shifts the corneal reflection positions of the bright and dark pupil image data by the differential position correction amount so that the corneal reflection positions match, adds the brightness of the image data thereto, and determines the resultant brightness centroid coordinates as the coordinates of the corneal reflection.

The image processor 7 further calculates a three-dimensional position of each of the left and right pupils of the subject A from the pupil center coordinates that are detected based on the image data output from the two cameras 2a, 2b. In so doing, the image processor 7 measures three-dimensional coordinates of each pupil by means of a stereo method. The stereo method is a method for previously measuring internal parameters such as the focal lengths of the lenses of the cameras, the centers of images, and pixel sizes, and external parameters such as the positions and orientations of the cameras, and then determining the spatial positions of points in images of a subject captured by a plurality of stereo cameras, based on the coordinates of the points by using the internal and external parameters.

Figure 3:
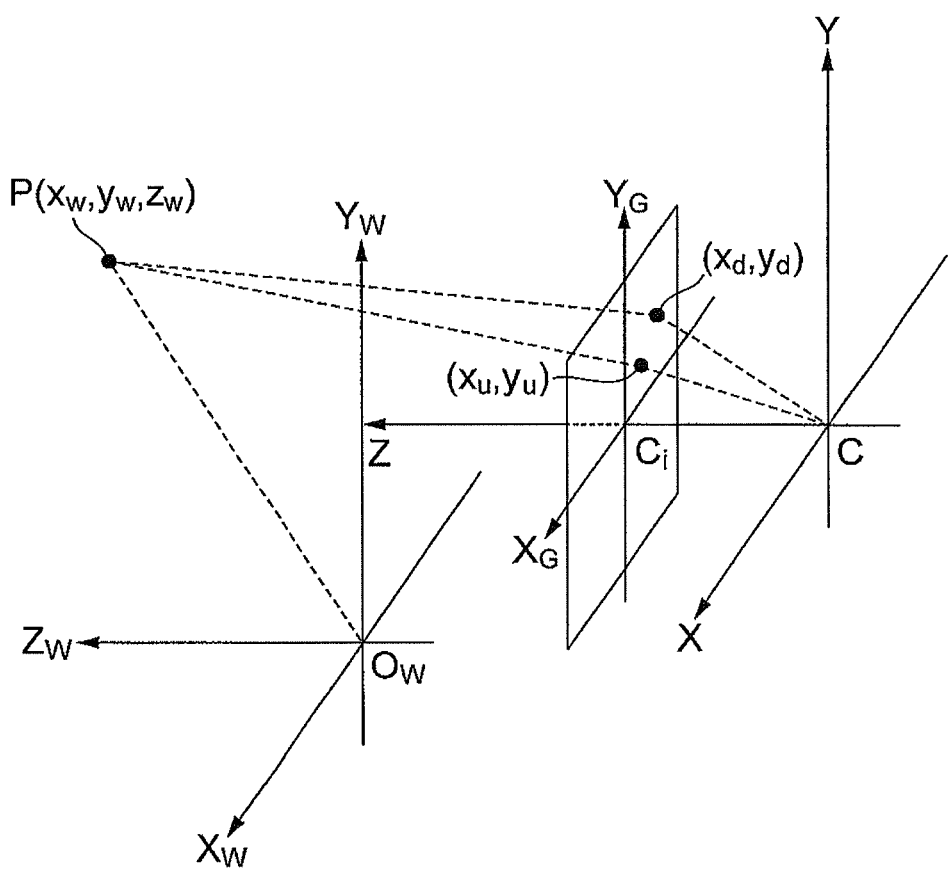
FIG. 3 is a diagram showing a positional relationship between coordinate systems set in the gaze point detection device shown in FIG. 1.

When the image processor 7 calculates the three-dimensional coordinates of the pupils by means of the stereo method, the coordinate system shown in FIG. 3 is used. A world coordinate system $(X_W, Y_W, Z_W)$ shown in the diagram is a coordinate system in which the origin $O_W$ thereof shared by the two cameras 2a, 2b is located in the middle of, for example, the screen of the display device 8. A camera coordinate system (X, Y, Z) is a coordinate system in which the origin C thereof is the optical center for the cameras 2a, 2b and the Z-axis is parallel to an optical axis extending from the optical center to be perpendicular to an image surface. An image coordinate system $(X_G, Y_G)$ is a coordinate system which is parallel to the XY plane along an image surface where image sensors are placed, and in which the intersection point (image center) of the optical axis and the image surface is taken as the origin $C_i$ of this coordinate system. Suppose that a point P is taken as a target point, a projected point $(X_d, Y_d)$ to be projected to the image coordinate system, which is obtained using the cameras 2a, 2b, is shifted from an ideal projected point $(X_u, Y_u)$ due to image distortion. Therefore, in order to accurately measure the three-dimensional positions using the stereo method, calibration data, in which the world coordinates of the target point P and the image coordinates thereof are associated with each other, need to be acquired in advance. Examples of such calibration data include, as the external parameters, a translation vector of the camera coordinate system with respect to the world coordinate system and a rotation matrix of the camera coordinate system with respect to the world coordinate system, and, as the internal parameters, the focal lengths, image center coordinates, scale factors, lens distortion coefficients, and an interval between pixels of the image sensor. Such calibration data are acquired beforehand and stored in the image processor 7.

In reference to the calibration data, the image processor 7 acquires relational expressions of pupil center coordinates in the image coordinate system and pupil center coordinates in the world coordinate system, the pupil center coordinates being detected based on the output data of the two cameras 2a, 2b. Subsequently, from these two relational expressions, the image processor 7 obtains three-dimensional position coordinates of the pupils of the subject A in the world coordinate system. The image processor 7 can also obtain the three-dimensional positions of the left and right pupils of the subject A in a similar manner.

The image processor 7 detects a point of gaze Q of the subject on the display device 8, by using the detected position of left or right corneal reflection point of the subject A and the position of the center of the corresponding pupil. A procedure for detecting the point of gaze Q by the image processor 7 is now described with reference to FIGS. 4 and 5; and a gaze point detection procedure in which only camera images obtained by the cameras 2a, 2b are used is described for simplification.

(Gaze Point Detection Procedure)

Figure 4:
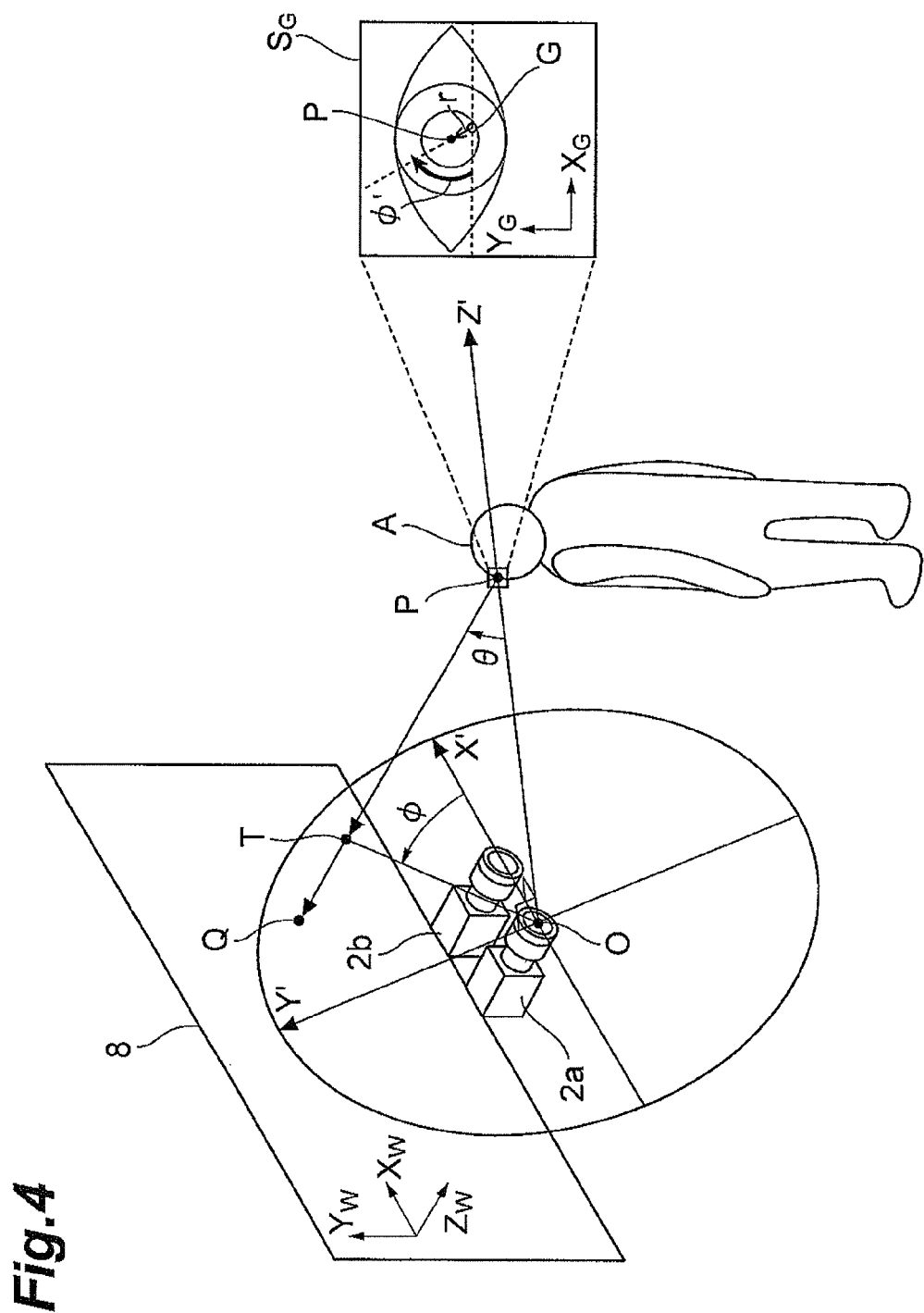
FIG. 4 is a diagram for explaining a gaze point detection procedure performed by the gaze point detection device shown in FIG. 1.

As shown in FIG. 4, based on the detected three-dimensional position P of the pupil, the center of each of the apertures 9a, 9b of the cameras 2a, 2b is taken as an origin O, and a virtual viewpoint plane X'-Y' is set in which a base line OP connecting the origin O and the pupil P is taken as the normal. Here, the X'-axis is the same as the intersection of an $X_W$-$Y_W$ plane of the world coordinate system and a virtual viewpoint plane X'-Y'.

First, the image processor 7 calculates a vector $r_G$ from a corneal reflection point G to the center of the pupil P in an image surface $S_G$. The vector $r_G$ is then converted into the vector r (a vector calculation step), which is the actual size that is obtained using the magnification of the cameras obtained based on the distance OP. In so doing, it is assumed that the cameras 2a, 2b are in the pinhole camera model and that the corneal reflection point G and the center of the pupil P exist on a plane parallel to the virtual viewpoint plane X'-Y'. In other words, on the plane that is parallel to the virtual viewpoint plane and includes the three-dimensional coordinates of the pupil P, the image processor 7 calculates relative coordinates of the center of the pupil P and the corneal reflection point G to obtain the vector r. The vector r represents the actual distance from the corneal reflection point G to the center of the pupil P.

Thereafter, in relation to a point of gaze T of the subject A located on the virtual viewpoint plane, the image processor 7 determines that an inclination $\phi$ of a straight line OT to the horizontal axis X' by setting equal to an inclination $\phi$ of the vector r to the horizontal axis $X_G$ on the image surface. The image processor 7 further uses the following formula (3) to calculate an angle $\theta$ formed between the base line OP and a line of sight vector of the subject A, a vector PT connecting the center of the pupil P and the point of gaze T (a line of sight direction calculation step):

$$\theta = f_1(r) = k \times |r - r_0| \quad (3)$$

where $f_1$ is a function using such parameters as a gain value k and an origin correction vector (offset vector) $r_0$.

The angles $\phi$, $\theta$ are calculated by considering that the enlarged vector r on the virtual viewpoint plane corresponds directly to the point of gaze of the subject A, the vector r before being enlarged existing on the plane having the center of the pupil P. More specifically, the angle $\theta$ of the line of sight PT of the subject A with respect to the base line OP is assumed to be in a linear relationship with the revised value $|r - r_0|$ of the distance between the center of the pupil and the corneal reflection. The origin correction vector $r_0$ of the function $f_1$ is set because the actual vector $r_0$ between the corneal reflection and the center of the pupil when the subject A looks at the cameras ($\theta=0$) is not equal to zero. Because the gain value k and the origin correction vector $r_0$ vary depending on the subjects A or their left and right eyeballs, the gain value k and the origin correction vector $r_0$ need to be calibrated. Thus, previously set initial values are corrected by a parameter correction process, which is described hereinafter, and then applied to the gain value k and the origin correction vector $r_0$.

Figure 5:
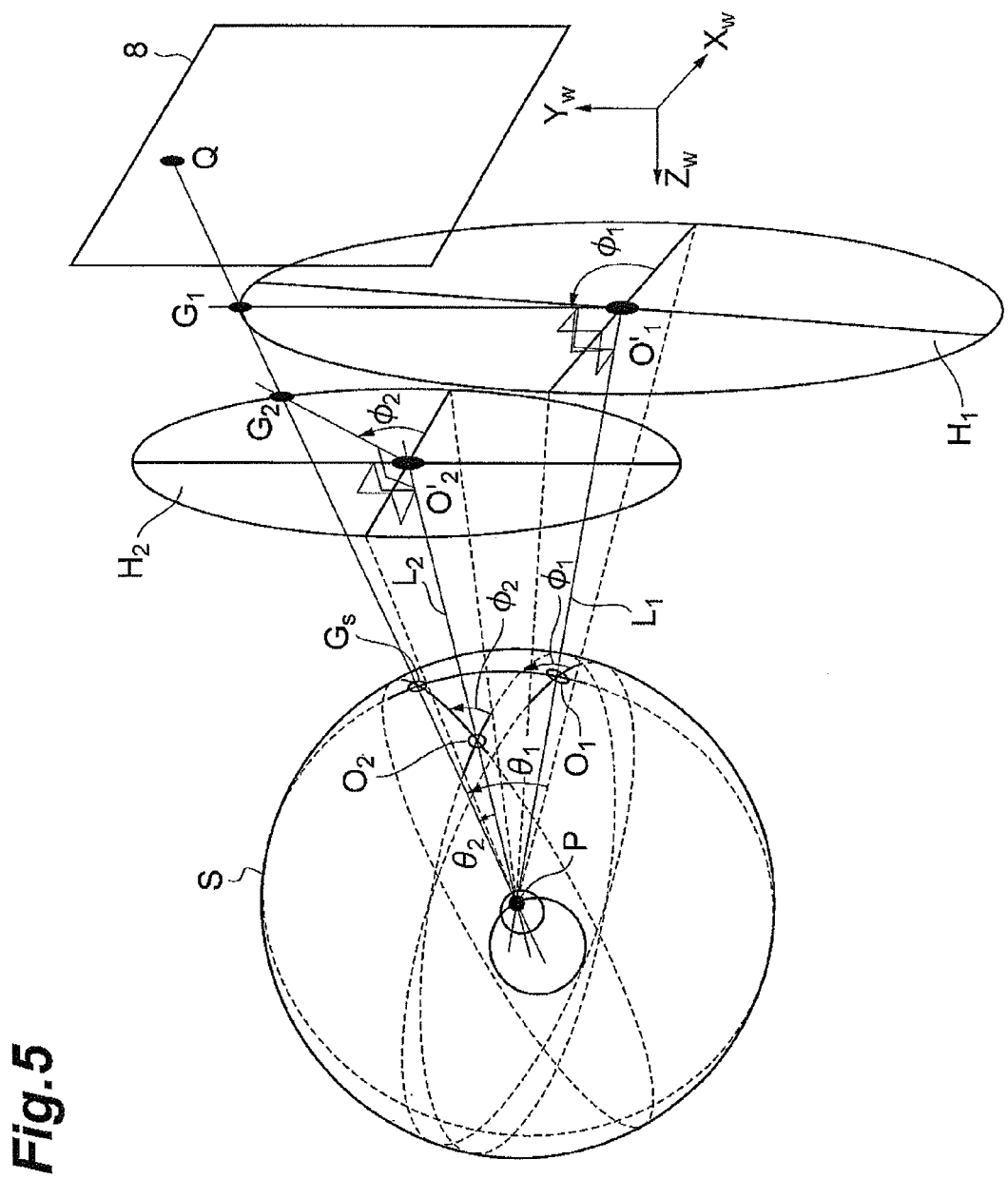
FIG. 5 is a diagram for explaining the gaze point detection procedure performed by the gaze point detection device shown in FIG. 1.

Furthermore, in reference to angles $\phi_1, \phi_2, \theta_1, \theta_2$ calculated as angles $\phi$, $\theta$ according to the camera images obtained by the two cameras 2a, 2b, the image processor 7 detects the point of gaze of the subject A on the screen of the display device 8 (a gaze point detection step). In so doing, a coordinate system shown in FIG. 5 is defined in order to describe a gaze point detection mechanism. Two virtual viewpoint planes $H_1$, $H_2$ with origins $O_1'$, $O_2'$ corresponding to the positions of the two cameras 2b, 2a and a virtual viewpoint spherical surface S with a random radius and the center of the pupil P, are defined. The two virtual viewpoint planes $H_1$, $H_2$ are perpendicular to straight lines $PO_1'$, $PO_2'$, respectively. The intersection point of the straight line (line of sight) extending between the center of the pupil P and the point of gaze Q on the display screen and the virtual viewpoint spherical surface S is taken as G the intersection point of the straight line extending between the center of the pupil P and the origin $O_1'$ and the virtual viewpoint spherical surface S as $O_1$, and the intersection point of the straight line extending between the center of the pupil P and the origin $O_2'$ and the virtual viewpoint spherical surface S as $O_2$. In a case where the intersection point of the line of sight PQ and the virtual viewpoint plane $H_1$ is $G_1$, the angle formed between a straight line $O_1'G_1$ and the horizontal axis of the virtual viewpoint plane $H_1$ becomes $\phi1$. Similarly, in a case where the intersection point of the line of sight PQ and the virtual viewpoint plane $H_2$ is $G_2$, the angle formed between a straight line $O_2'G_2$ and the horizontal axis of the virtual viewpoint plane $H_2$ becomes $\phi_2$. In addition, on the virtual viewpoint spherical surface S, the angle formed between a curve $O_1G_S$ and the intersection (curve) of the spherical surface S and the horizontal plane extending through the point $O_1$ is equal to the angle $\phi_1$. Similarly, on the virtual viewpoint spherical surface S, the angle formed between a curve $O_2G_S$ and the intersection (curve) of the spherical surface S and the horizontal plane extending through the point $O_2$ is equal to the angle $\phi_2$. Because, as described above, the points P, $O_1$, $O_1'$ exist on the same straight line $L_1$ and the points P, $O_2$, $O_2'$ exist on the same straight line $L_2$, the angle between the straight line $L_1$ and the line of sight becomes $O_1$ and the angle between the straight line $L_2$ and the line of sight becomes $O_2$.

The image processor 7 can calculate the point of gaze on the screen by using the above-described relationships with reference to the data on the previously known position coordinates of the origins $O_1'$, $O_2'$ and the position and orientation of the display device 8. In other words, the image processor 7 can acquire a relative positional relationship between the points $G_S$, $O_1$, $O_2$ on the virtual viewpoint spherical surface S from the angles $\phi_1, \phi_2, \theta_1, \theta_2$ that are calculated by the camera images captured by the two cameras 2a, 2b. The image processor 7, therefore, can uniquely obtain a line of sight $PG_S$ from the known coordinates of the origins $O_1'$, $O_2'$ and the calculated coordinate of the center of the pupil P, and detect the point of gaze Q by calculating the intersection point of the line of sight $PG_S$ and the screen of the display device 8. In a case where the line of sight $PG_S$ obtained from the angles $\phi_1$, $\theta_1$ and the gaze PGS obtained from the angles $\phi_2, \theta_2$ are out of alignment, the average of these lines of sight can be calculated as a final line of sight vector.

The function $f_1$ used by the image processor 7 in the line of sight direction calculation step includes the gain value k and the origin correction vector $r_0$ as the parameters. As is clear from the formula (3), this gain value k is a magnification used for obtaining the angle $\theta$ of the line of sight direction from the vector r between the corneal reflection and the center of the pupil, based on the assumption that the length of the vector $(r-r_0)$, which is the adjusted vector r, and the angle $\theta$ are in a linear relationship. Ideally, as long as the angle $\theta$ and the vector |r| are in the linear relationship, the angle $\theta$ should be calculated by simply obtaining the gain value k. In other words, when the angle $\theta$ is zero, in other words, when the subject A gazes at the cameras, the vector |r| should be equal to zero. However, when the visual axis (gaze) of the eyeball actually does not match the optical axis and moreover the angle $\theta$ is equal to zero, the vector |r| is a value other than 0. Furthermore, when the subject A is changed to another subject and the angle $\theta$ is equal to zero, the value of the vector |r| changes.

Figure 6:
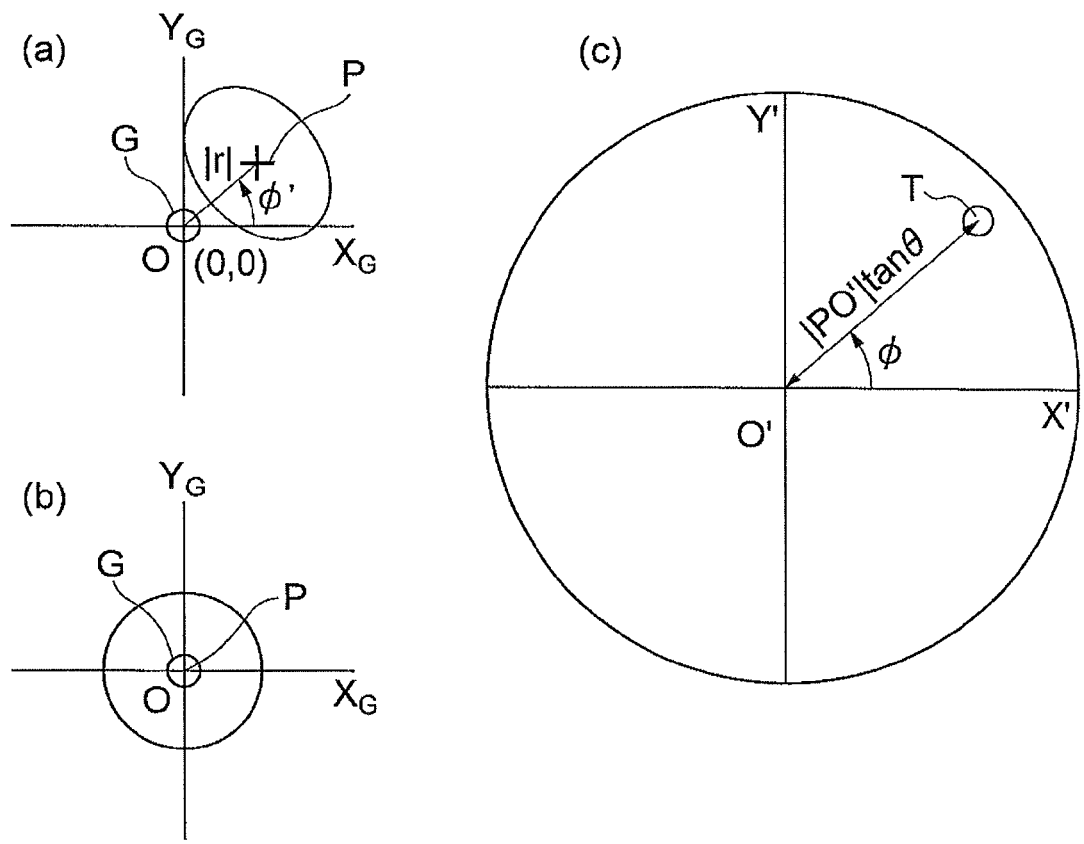
FIG. 6(*a*) and FIG. 6(*b*) are diagrams showing vectors r observed in the camera image, and FIG. 6(*c*) is a diagram showing a point of gaze T on a virtual viewpoint plane.
Figure 7:
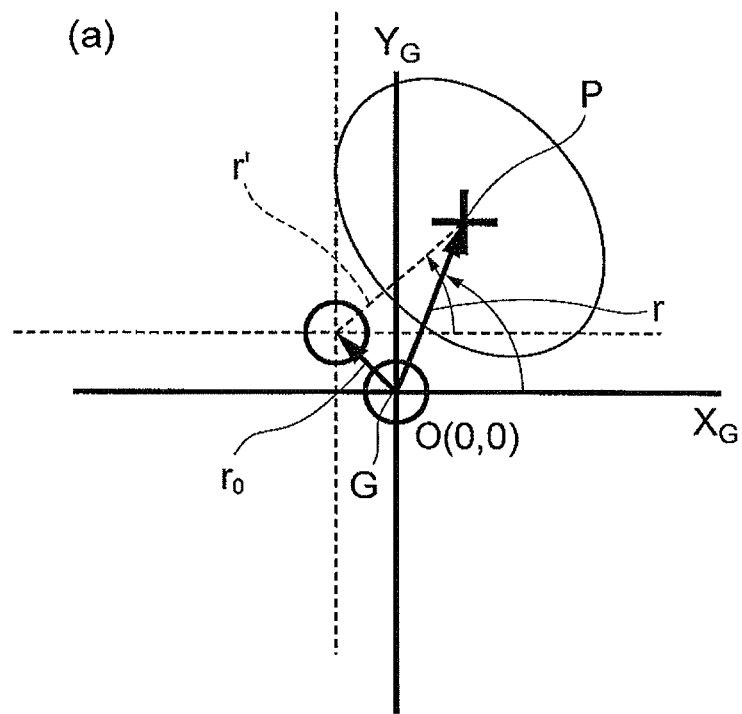
FIG. 7 is a diagram showing the vector r that is observed on an image captured by the camera shown in FIG. 1.
Figure 7:
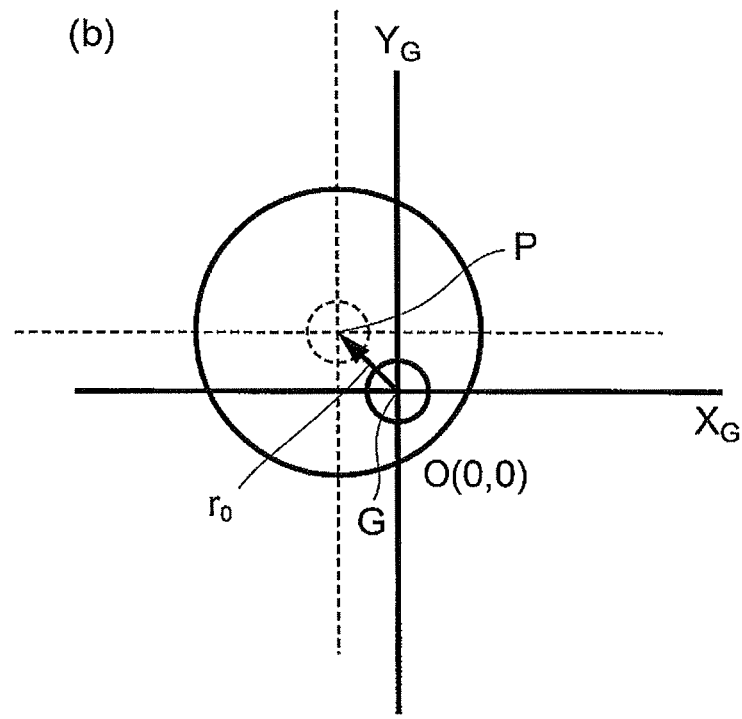

This phenomenon is now described with reference to FIGS. 6 and 7. FIG. 6(c) shows the point of gaze T on the virtual viewpoint plane that includes the position O' of each camera. FIGS. 6(a), 6(b) and FIGS. 7(a), 7(b) each show the vector r that is observed on the image captured by each camera. The length of a segment O'T on the virtual viewpoint plane can be calculated using a formula, |O'T|=|PO'| tan $\theta$. When the subject A looks at the cameras, ideally, the positions of the center of the pupil P and the corneal reflection G caught on the cameras match (FIG. 6(b)). On the other hand, when the subject A looks at the point of gaze T, the position of the center of the pupil P is shifted from the corneal reflection G (FIG. 6(a)). At this moment the angle $\phi'$ on the camera images becomes equal to the angle $\phi$ on the virtual viewpoint plane. When, however, the subject A actually looks at the cameras, the center of the pupil P and the corneal reflection point G on the camera images do not match. For instance, as shown in FIG. 7(b), the corneal reflection point G is shifted to the lower right side of the center of the pupil P. As shown in FIG. 7(a), on the other hand, when the subject A looks at the point of gaze T, the center of the pupil P is further shifted from the corneal reflection G FIGS. 7(a), 7(b) each show a coordinate system in the dotted lines in which the center of the pupil P of the subject A looking at each camera is taken as the origin of the coordinate system. It is considered that, by calculating a position vector r' of the center of the pupil P in each coordinate system, an ideal relationship between the center of the pupil P and the corneal reflection G shown in FIG. 6 can be established in relation to the vector r'. In other words, when the subject A looks at the cameras, the position vector $r_0$ of the center of the pupil P is obtained with the corneal reflection G as the origin. Then, based on this position vector $r_0$ and the vector r in the eye of the subject A looking at the point of gaze T, the vector r' is obtained using the following formula (4) (FIG. 7(a)):

$$r'=r-r_0 \qquad (4).$$

In addition, based on the obtained vector r', not only is it possible to obtain the correct angle $\theta$ by applying the gain value k, but also the angle $\phi$ can be obtained from the vector r'. This vector $r_0$ is the origin correction vector.

Because the parameters k, $r_0$ described above vary depending on the subjects A, the parameters need to be calibrated beforehand. In other words, the parameters k, $r_0$ are undetermined constants in the early stage after activation of the device; thus, appropriate values need to be predetermined by calibrating the parameters, in order to accurately detect the line of sight. A parameter correction procedure that is executed by the image processor 7 prior to the gaze point detection process is now described hereinafter.

(Parameter Correction Procedure, Undetermined Constant Determination Step)

Figure 8:
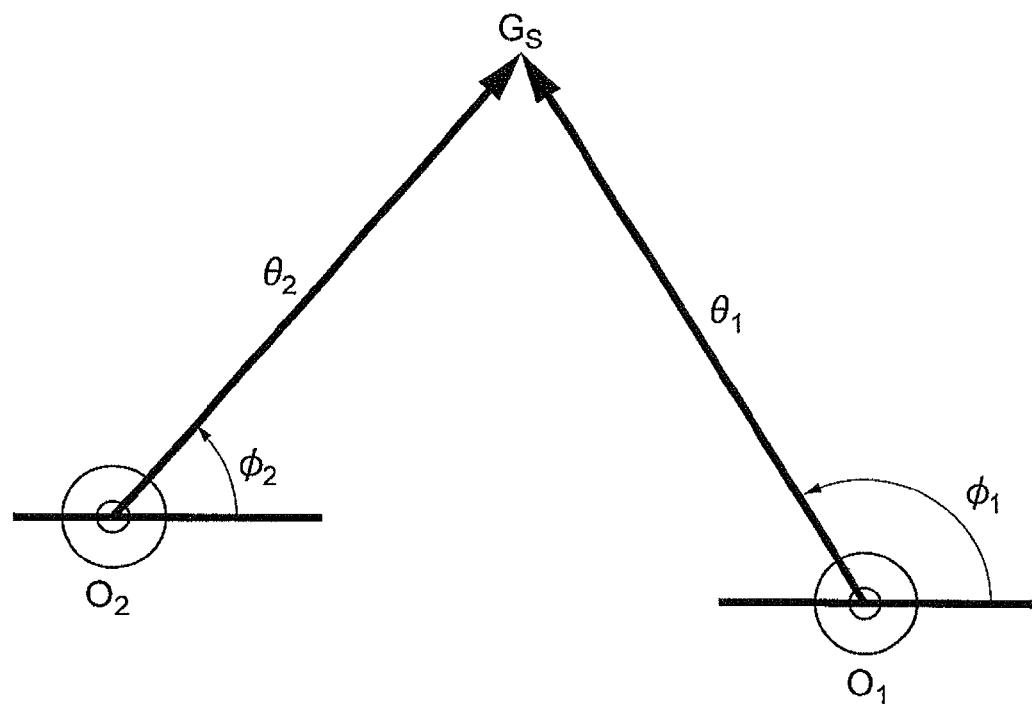
FIG. 8 is a diagram in which points $O_1$, $O_2$ and $G_S$ that are projected on a virtual viewpoint spherical surface S of FIG. 5 are further projected on a plane.

FIG. 8 is a diagram in which the points $O_1$, $O_2$, $G_S$ projected on the virtual viewpoint spherical surface S of FIG. 5 are further projected onto a plane. Vectors $\theta_1$, $\theta_2$ shown in the diagram represent the angles of the line of sight. The vectors $r_1$, $r_2$ are the actual distances between the corneal reflection and the centers of the pupils, which are calculated from the images that are captured by the cameras 2a, 2b when the subject looks at the point $G_S$ on the virtual viewpoint spherical surface S. Based on a formula $r_0=(x_0, y_0)$ where $r_0$ is the vector between the corneal reflection and the center of each pupil in the eye of the subject A looking at the points $O_1$, $O_2$, $O_1'$, $O_2'$ in the direction of the cameras, the vectors $r_1'$, $r_2'$, obtained after correcting the origins of the vectors $r_1$, $r_2$, are expressed by the following formula (5):

$$r_1' = r_1 - r_0$$

$$r_2' = r_2 - r_0 \quad (5).$$

In addition, the relationships expressed by the following formula (6) can be obtained from the formula (3):

$$\theta_1 = k|r_1 - r_0|$$

$$\theta_2 = k|r_2 - r_0| \quad (6).$$

Figure 9:
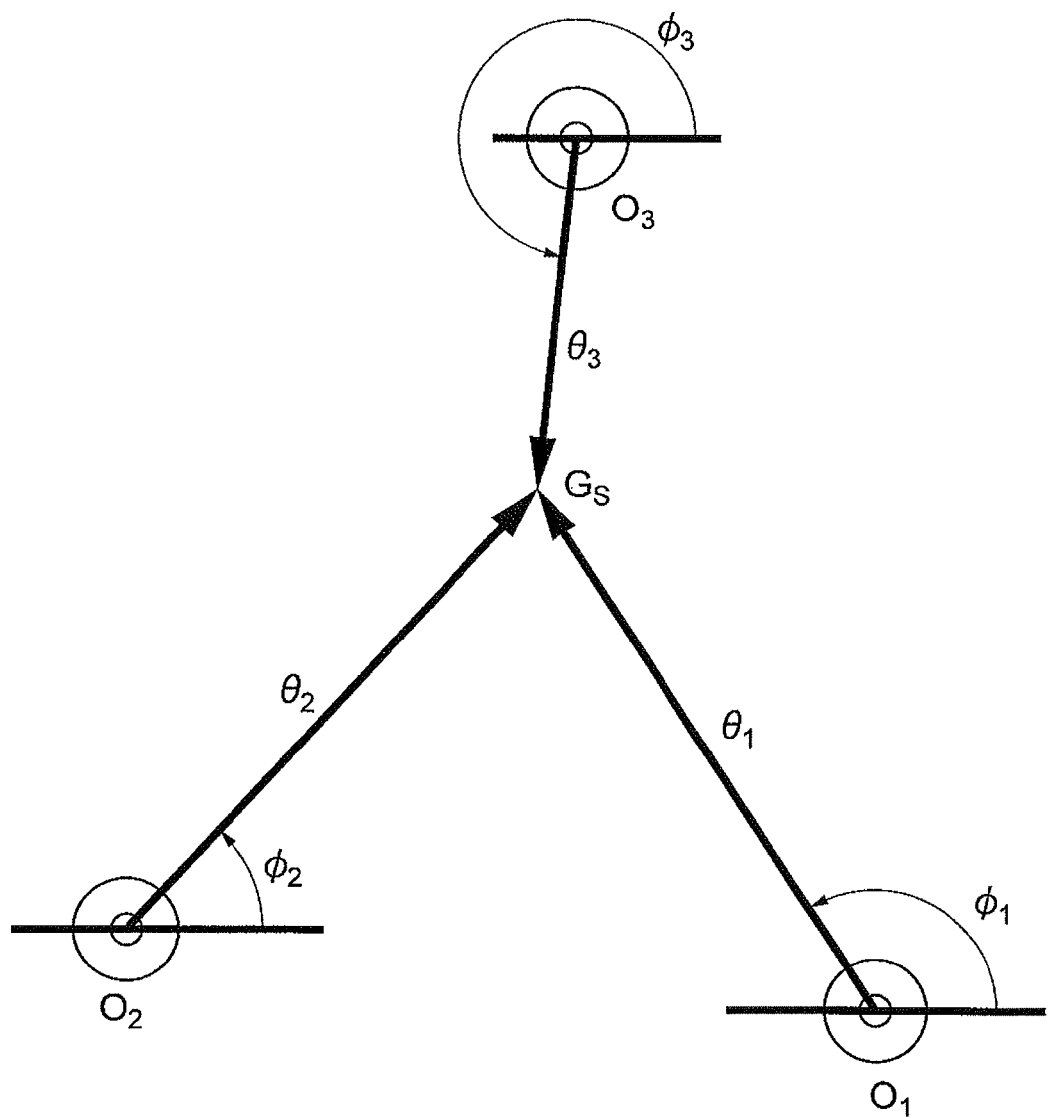
FIG. 9 is a diagram in which points $O_1$, $O_2$, $O_3$ and $G_S$ that are projected on the virtual viewpoint spherical surface S shown in FIG. 5 are further projected on a plane.

In this case, while causing the subject A to gaze at one specified point on the screen of the display device 8, the coordinate of the specified point being known, the image processor 7 accordingly detects the vector $r_1=(x_1, y_1)$ and the vector $r_2=(x_2, y_2)$. The angles $\theta_1$, $\theta_2$ of line of sight can be calculated from the specified point and applied to the formula (6) together with the vectors $r_1$, $r_2$ in the two relational expressions, so that the two relational expressions have three unknown parameters k, $x_0$, $y_0$. Thus, it is sufficient to establish three or more relational expressions in order to obtain these unknown parameters. In this case, the image processor 7 further detects a vector $r_3=(x_3, y_3)$ between the corneal reflection and the center of the pupil by using a camera image that is captured by either the camera 2c or the camera 2d when the subject A gazes at one specified point (FIG. 9). The vector $r_3$ and angle $\theta_3$ are substituted into the following formula (7) to derive a third relational expression:

$$\theta_3 = k|r_3 - r_0| \quad (7).$$

By establishing simultaneous equations with the three relational expressions, the image processor 7 can calculate the parameters k, $x_0$, $y_0$ and store these parameters as the correction values. Although the gaze point detection device 1 is provided with the four cameras 2a, 2b, 2c, 2d and the four light sources 3a, 3b, 3c, 3d as shown in FIG. 1, at least three cameras and three light sources may be enough to realize the parameter correction process.

The parameter correction process described above is executed on thirty frames of camera images obtained within a period of approximately 1 second, and the average value of parameters calculated with respect to frames is stored as the correction value.

In the line of sight direction calculation step, the image processor 7 may use, in place of the formula (3) described above, a function $f_2$ having a non-linear relationship between a vector |r'| and the angle $\theta$ shown in the following formula (8):

$$\theta = f_2(r) = k|r'| + h|r'|^4 \quad (8).$$

With up to approximately 20 degrees of the angle $\theta$ of line of sight, the linearity of the formula (3) is established; however, non-linearity is more likely to occur with respect to most subjects A when the angle $\theta$ reaches approximately 30 degrees. In this case, because there are four unknown parameters k, h, $x_0$, $y_0$ as the unknown parameters, the image processor 7 requires four or more relational expressions in order to realize the parameter correction process. Thus, using the images that are captured by the four cameras 2a, 2b, 2c, 2d when the subject A gazes at one specified point, the image processor 7 detects a vector $r_i=(x_i, y_i)$ (i=1 to 4) and substitutes the vector $r_i$ and angle $\theta_i$ into the formula (8) to derive four relational expressions. Then, the image processor 7 can establish simultaneous equations with the four relational expressions, thereby calculating the four parameters k, h, $x_0$, $y_0$ and storing the calculated parameters as the correction values. In other words, in order to correct the parameters in this case, at least four pairs of cameras and light sources are required.

Moreover, in the line of sight direction calculation step, the image processor 7 may use, in place of the formula (8) described above, a formula that includes a plurality of other non-linear terms such as the square or cube of |r'|, or may set the multipliers of the non-linear terms as undefined parameters. In this case as well, a predetermined number or more cameras are set in the gaze point detection device 1 in order to derive as many relational expressions as not less than the number of parameters requiring correction.

Note that, when correcting the parameters, the specified points at which the subject A is caused to look are preferably not positioned equally away from the cameras but positioned different distances from the cameras in order to deal with non-linear functions. In this case, when the subject A looks at, for example, the right end or the like of the display screen, the distances from each camera to the right end vary from one another; therefore, the non-linear parameters can be obtained accurately, improving the calibration accuracy.

(Other Parameter Correction Procedures)

Figure 10:
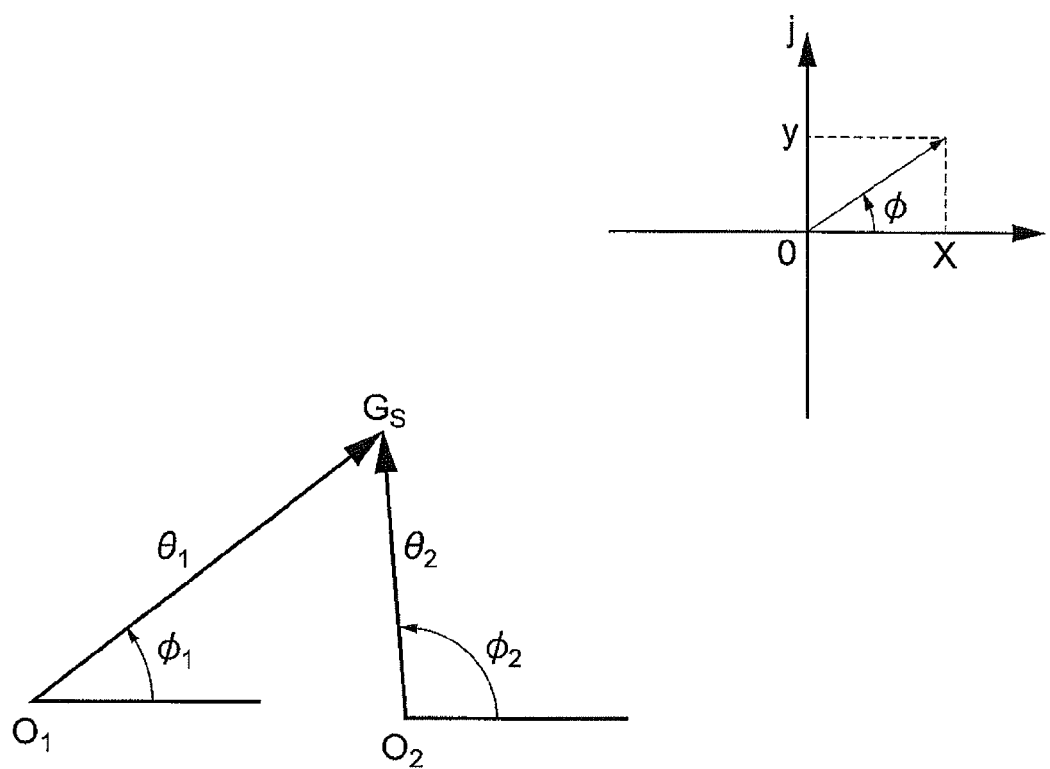
FIG. 10 is a diagram showing an angle $\theta_i$ as a vector on a projection drawing in which a point is projected onto a plane of the virtual viewpoint spherical surface S shown in FIG. 8.

In the parameter correction procedure described above, the angle $\theta_i$ is used as a scalar quantity to correct the parameters, but the angle $\theta_i$ may be used as a vector. FIG. 10 shows the angle $\theta_i$ as a vector on a projection drawing in which a point of the virtual viewpoint spherical surface S is projected onto the plane shown in FIG. 8. FIGS. 11(a) and 11(b) show, respectively, the vectors $r_i$, $r_i'$ (i=1, 2) that are detected on the camera images captured by the two cameras 2b, 2a. The vectors $r_1$, $r_2$ are directly detected from the camera images by the image processor 7, and vectors $r_{10}$, $r_{20}$ are the origin correction vectors corresponding to the camera images respectively.

Figure 11:
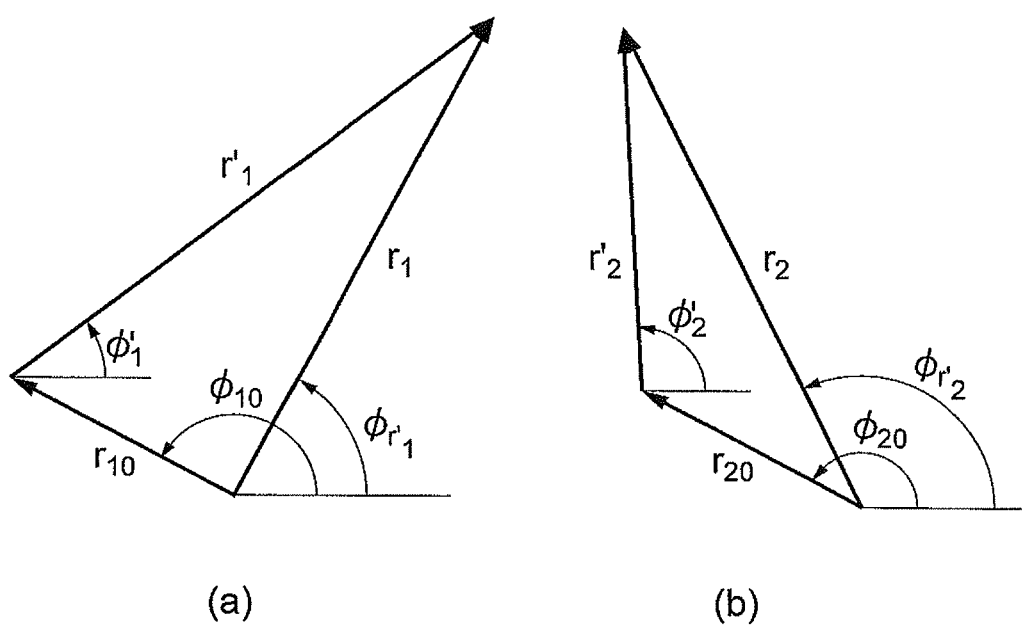
FIG. 11 is a diagram showing vectors $r_i$ and $r_i'$ detected on the camera image of the camera shown in FIG. 1.

The x-axes and y-axes of the two-dimensional spaces shown in FIGS. 10 and 11 are associated with real number axes and imaginary number axes on complex planes, wherein "j" in the diagrams represent the imaginary unit. The relationship of inclinations $\phi_1'$, $\phi_2'$ of the vectors $r_1'$, $r_2'$ obtained after origin correction to the angles $\phi_1$, $\phi_2$ on the virtual viewpoint plane is as follows: $\phi_1=\phi_1'$, $\phi_2=\phi_2'$. The vector $\theta_1$ is parallel to the vector $r_1'$, and the vector $\theta_2$ is parallel to the vector $r_2'$; thus, the following formulae (9) and (10) are established.

[Formula 1]

$$r_1' = s\theta_1 = s|\theta_1|e^{j\phi_1'} = |r_1'|e^{j\phi_1'} = |r_1'|(\cos\phi_1' + j\sin\phi_1'), \quad (9)$$

-continued $$r_2' = s\theta_2 = s|\theta_2|e^{j\phi_2'} = |r_2'|e^{j\phi_2'} = |r_2'|(\cos\phi_2' + j\sin\phi_2') \text{ where, } s > 0$$

[Formula 2]

$$r_1 = |r_1|e^{j\phi_{r_1}} = |r_1|(\cos\phi_{r_1} + j\sin\phi_{r_1}), \quad (10)$$

$$r_2 = |r_2|e^{j\phi_{r_2}} = |r_2|(\cos\phi_{r_2} + j\sin\phi_{r_2})$$

In addition, the origin correction vectors $r_{10}$, $r_{20}$ are expressed in the following formulae (11) and (12).

[Formula 3]

$$r_{10} = r_1 - r_1' = |r_1|(\cos\phi_{r_1} + j\sin\phi_{r_1}) - \quad (11)$$
$$|r_1'|(\cos\phi_1' + j\sin\phi_1')$$
$$= |r_1|(\cos\phi_{r_1} + j\sin\phi_{r_1}) -$$
$$s|\theta_1|(\cos\phi_1' + j\sin\phi_1')$$

[Formula 4]

$$r_{20} = r_2 - r_2' = |r_2|(\cos\phi_{r_2} + j\sin\phi_{r_2}) - \quad (12)$$
$$|r_2'|(\cos\phi_2' + j\sin\phi_2')$$
$$= |r_2|(\cos\phi_{r_2} + j\sin\phi_{r_2}) -$$
$$s|\theta_2|(\cos\phi_2' + j\sin\phi_2')$$

Here, the origin correction vectors $r_{10}$, $r_{20}$ are considered to be equal to each other as a result of the detection by the two cameras. Thus, the following two relational expressions (13), (14) are derived from the relationship: $r_{10}=r_{20}=r_0$. Because a parameter s is the only unknown parameter in the formulae (13) and (14), the image processor 7 can calculate the parameter s from each of these formulae and obtain the average value of the calculated parameters as the correction value. The image processor 7 can also substitute the determined parameter s into the formula (11) to determine the origin correction vector $r_0$.

[Formula 5]

$$|r_1|\cos\phi_{r_1}' - |r_2|\cos\phi\phi_{r_2}' = s(|\theta_1|\cos\phi\phi_{r_1}' - |\theta_2|\cos\theta\phi_{r_2}') \quad (13)$$

[Formula 6]

$$|r_1|\sin\phi_{r_1}' - |r_2|\sin\phi\phi_{r_2}' = s(|\theta_1|\sin\phi\phi_{r_1}' - |\theta_2|\sin\theta\phi_{r_2}') \quad (14)$$

In other words, in relation to the four relational expressions that take into account the real number components and imaginary number components of the formulae (11) and (12), there are three unknown parameters: two components of the origin correction vector $r_0$ and the parameter s which is a reciprocal number of the gain value k. The image processor 7 can therefore calculate and determine the three parameters as the correction values, based on the camera images that are captured by at least the two cameras when the subject A gazes at one specified point.

In this case as well, in the line of sight direction calculation step, the image processor 7 may use a function having a non-linear relationship between the vector and the angle $\theta_i$. Specifically, the following formula (15) is used in place of the formula (9):

$$|r_i'|=s|\theta_i|-t|\theta_i|^4 \quad (15).$$

On the basis of such non-linear function, the origin correction vectors $r_{10}$, $r_{20}$ are calculated by the following formulae (16) and (17):

[Formula 7]

$$r_{10}=r_1-r_1'=|r_1|(\cos\phi_{r_1}'+j\sin\phi_{r_1}')-(s|\theta_1|-t|\theta_1|^4)(\cos\phi_1'+j\sin\phi_1') \quad (16); \text{ and}$$

[Formula 8]

$$r_{20}=r_2-r_2'=|r_2|(\cos\phi_{r_2}'+j\sin\phi_{r_2}')-(s|\theta_2|-t|\theta_2|^4)(\cos\phi_2'+j\sin\phi_2') \quad (17).$$

In relation to the four relational expressions that take into account the real number components and imaginary number components in the formulae (16) and (17), there are four unknown parameters: two components of the origin correction vector $r_0$ and the parameters s, t. The image processor 7 can therefore calculate and determine the four parameters as the correction values in consideration of the non-linear elements, based on the camera images that are captured by at least the two cameras when the subject A gazes at one specified point.

The image processor 7 can further correct the parameters as follows instead of using the formulae (11) and (12). In other words, the vector $\theta_i$ is provided by the following formula (18) using the relationship among the origin correction vectors $r_{10}=r_{20}=r_0$.

[Formula 9]

$$\theta_1=kr_1'=k(r_1-r_0),$$

$$\theta_2=kr_2'=k(r_2-r_0) \quad (18)$$

In addition, the following formula (19) is obtained with reference to FIG. 10.

[Formula 10]

$$\theta_1-\theta_2=\overrightarrow{O_1O_2} \quad (19)$$

The right side of the formula (19) expresses vectorized angle $O_1PO_2$. In relation to the four relational expressions that take into account the real number components and imaginary number components in the formula (18), there are three unknown parameters: two components of the origin correction vector $r_0$ and the parameter k. The image processor 7 can therefore calculate and determine the three parameters as the correction values, based on the camera images that are captured by at least the two cameras when the subject A gazes at one specified point.

It is understood that, in order to accurately determine the undetermined constants through the various parameter correction procedures, at least M×½ (rounded up) cameras or more are required, M being the number of undetermined constants.

According to the gaze point detection device 1 and the gaze point detection method using the gaze point detection device 1, face images of the subject A are generated by the four cameras 2a, 2b, 2c, 2d and the light sources 3a, 3b, 3c, 3d provided outside the apertures of the cameras, and, based on each of the face images, the vector $r_i$ (i=1 to 4) from the corneal reflection point of the subject to the center of each pupil is calculated for each of the four cameras 2a, 2b, 2c, 2d. The angle $\theta_i$ of each line of sight of the subject A to the base line is calculated for each of the four cameras by applying each of the calculated vectors $r_i$ to a function. Further, as many relational expressions as not less than the number of unknown parameters are derived based on the angles $\theta_i$ calculated in the manner described above, and the parameters included in the functions are corrected using these relational expressions. Subsequently, the line of sight direction and the point of gaze Q are detected from the face images of the subject A by using the corrected functions. As a result, automatic correction on the functions for calculating the line of sight directions can be executed with a high degree of accuracy, without requiring the subject A to gaze at a plurality of specified points or the apertures of the cameras. This can consequently reduce the burden on the subject and detect the point of gaze at high speed and with a high degree of accuracy. Because the functions and the origin correction vector $r_0$ are corrected, and consequently the correct gain value k is obtained, the angle $\theta_i$ of line of sight can be calculated accurately throughout the entire display screen where the viewpoint of the subject is detected.

For example, the parameters k, $r_0$ of the function $f_1$ can be corrected by allowing the subject A to gaze at a plurality of specified points including the apertures of the cameras. This is, however, a burden for the subject A to be required to carefully stare at two or more points. It is also difficult to instruct the subject A to look at a plurality of specified points sequentially, or it is difficult to determine which specified point the subject actually looks at, resulting in inaccurate parameter calibration. It is also difficult to actually cause the subject to look at the apertures of the cameras, and, consequently, the correction value of the parameter $r_0$ cannot be obtained accurately. As a result, the margin of error on the correction value of the gain value k expands, and the difference between the point at which the subject A actually gazes and the position of the point of gaze to be detected (gaze point detection error) changes depending on an target position, making the subsequent re-correction complicated. According to the present embodiment, however, the burden on the subject A can be reduced by simply allowing the subject to look at one specified point, and the gaze point detection error can be reduced over the entire display screen because it is not necessary to cause the subject to look at the apertures of the cameras.

The gaze point detection device 1 and the gaze point detection method according to the present embodiment can be applied to an autism diagnosis support system for a test subject by determining the difference in ratio between a time period during which the test subject looks into the eyes of the opposing person or of a person appearing on the display and a time period during which the test subject looks elsewhere.

Note that the present invention is not limited to the embodiment described above. For example, the gaze point detection method according to the present invention can employ various other aspects of the parameter correction procedure. For instance, the image processor 7 can complete parameter calibration by executing the following parameter calibration procedure, while the subject A looks at not a predetermined specified point but an adequate position.

Figure 12:
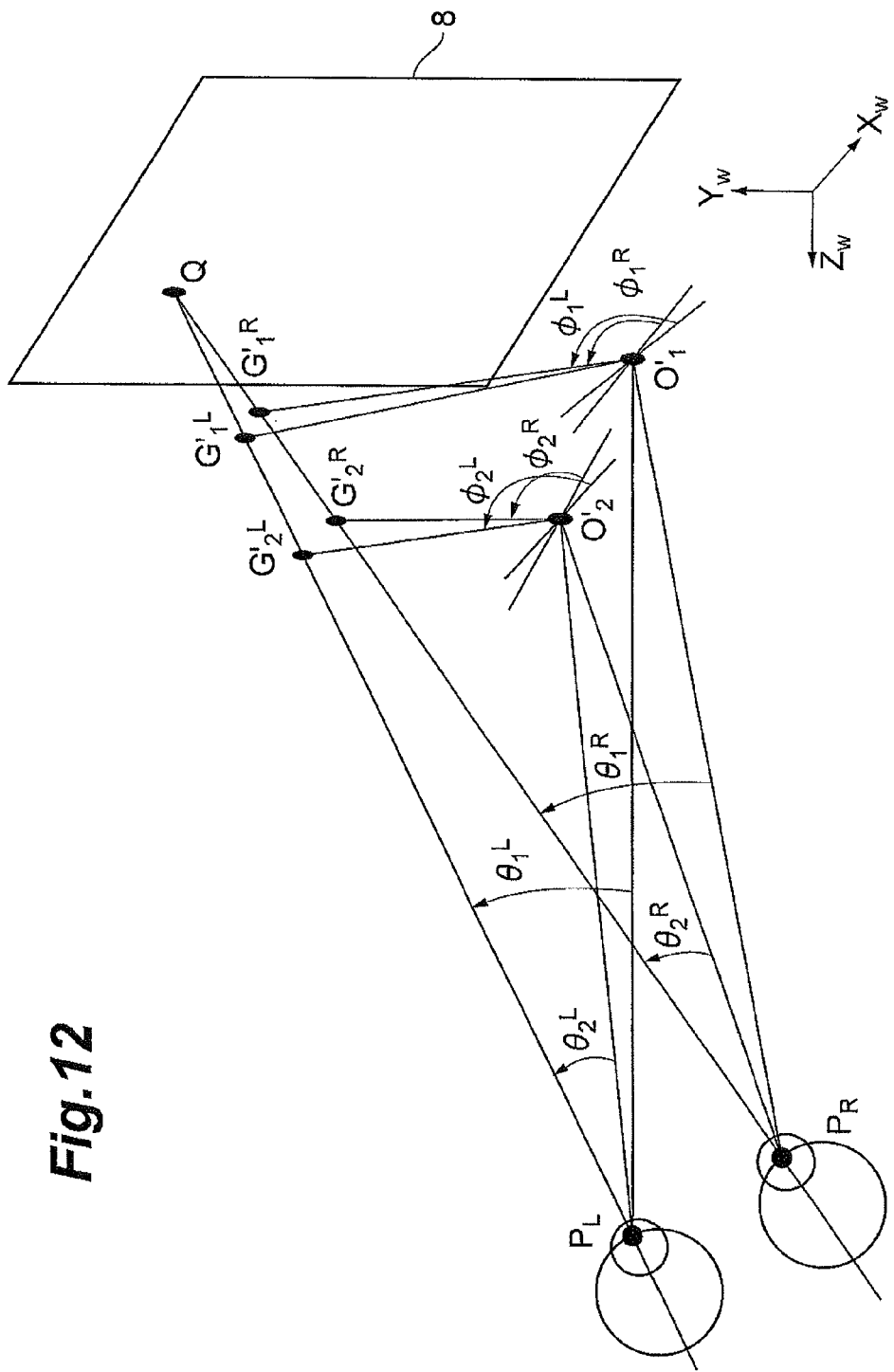
FIG. 12 is a diagram showing a positional relationship of the left and right pupils of a subject A to a point of gaze Q on a screen of a display device 8.

FIG. 12 is a diagram that shows the positional relationship between the point of gaze Q on the screen of the display device 8 and the left and right pupils of the subject A in order to explain the parameter calibration procedure. In this diagram, $P_L$ and $P_R$ respectively represent center coordinates of the left pupil and the right pupil, and the point of gaze Q is a point at which the both eyes of the subject A looks. In other words, the straight lines $P_L Q$ and $P_R Q$ represent the visual axes of the left and right eyes respectively. Points $G_1'^L$ and $G_2'^L$ on the straight line $P_L Q$ and points $G_1'^R$ and $G_2'^R$ on the straight line $P_R Q$ represent the intersection points of two virtual viewpoint planes including the positions $O_1'$ and $O_2'$ of the cameras 2b, 2a and these straight lines. The angles $\theta$ of line of sight which are detected in accordance with the left and right eyeballs of the subject A are expressed as $\theta_1^L$, $\theta_1^R$ $\theta_2^L$, $\theta_2^R$, and the gain values k and the origin correction vectors $r_0$ as $k_L$, $k_R$, and $r_0^L$, $r_0^R$ in accordance with the left and right eyeballs.

In such a case, the image processor 7 can calculate the angle $\theta_1^R$ using the following formula (20):

[Formula 11]

$$\theta_1^R = k_R |r_1^R| = k_R |r_1^R - r_0^R| \qquad (20)$$

The following relational expression (21) can be derived using the angle $\theta_1^R$ and the inner product of vectors $P_R Q$ and $P_R O_1'$:

[Formula 12]

$$\cos\theta_1^R = \frac{\left(\overrightarrow{P_R Q}, \overrightarrow{P_R O_1'}\right)}{|\overrightarrow{P_R Q}||\overrightarrow{P_R O_1'}|}. \qquad (21)$$

The following relational expression (22) can also be derived from these formulae (20) and (21):

[Formula 13]

$$\cos(k_R |r_1^R - r_0^R|) = \frac{\left(\overrightarrow{P_R Q}, \overrightarrow{P_R O_1'}\right)}{|\overrightarrow{P_R Q}||\overrightarrow{P_R O_1'}|}. \qquad (22)$$

The following formulae (23) to (25) are derived similarly for the angles $\theta_1^L$, $\theta_2^R$ and $\theta_2^L$:

[Formula 14]

$$\cos(k_R |r_2^R - r_0^R|) = \frac{\left(\overrightarrow{P_R Q}, \overrightarrow{P_R O_2'}\right)}{|\overrightarrow{P_R Q}||\overrightarrow{P_R O_2'}|}; \qquad (23)$$

[Formula 15]

$$\cos(k_L |r_1^L - r_0^L|) = \frac{\left(\overrightarrow{P_L Q}, \overrightarrow{P_L O_1'}\right)}{|\overrightarrow{P_L Q}||\overrightarrow{P_L O_1'}|}; \text{ and} \qquad (24)$$

[Formula 16]

$$\cos(k_L |r_2^L - r_0^L|) = \frac{\left(\overrightarrow{P_L Q}, \overrightarrow{P_L O_2'}\right)}{|\overrightarrow{P_L Q}||\overrightarrow{P_L O_2'}|}. \qquad (25)$$

As illustrated above, the four relational expressions can be derived based on the camera images captured by the two cameras, the four relational expressions including eight unknown parameters: $k_L$, $k_R$, $r_0^L = (x_0^L, y_0^L)$, $r_0^R = (x_0^R, y_0^R)$, and the two-dimensional coordinates of the point of gaze Q. Therefore, using the constraint condition that the points of gaze Q of the left and right eyes of the subject A matches each other on the display screen, the image processor 7 can derive eight relational expressions based on the camera images captured by the four cameras 2a, 2b, 2c, 2d, calculate parameters based on these relational expressions, and determine the parameters as the correction values. In this case as well, the number of cameras is set at at least 8×½=4 so that the undetermined constants are properly determined by the parameter correction procedure.

The image processor 7 also can execute parameter correction using a relational expression derived by taking angles $\theta_i^L$, $\theta_i^R$ as vectors. Specifically, as to the relationship between $r_1'^R$ and $\theta_1^R$, the following formulae (26) and (27) are derived:

[Formula 17]

$$r_1'^R = s_R \theta_1^R = s_R |\theta_1^R| e^{j\phi_1'^R} = |r_1'^R|(\cos\phi_1'^R + j\sin\phi_1'^R); \text{ and} \quad (26)$$

[Formula 18]

$$r_2'^R = s_R \theta_2^R = s_R |\theta_2^R| e^{j\phi_2'^R} = |r_2'^R|(\cos\phi_2'^R + j\sin\phi_2'^R),$$

$$r_1'^L = s_L \theta_1^L = s_L |\theta_1^L| e^{j\phi_1'^L} = |r_1'^L|(\cos\phi_1'^L + j\sin\phi_1'^L),$$

$$r_2'^L = s_L \theta_2^L = s_L |\theta_2^L| e^{j\phi_2'^R} = |r_2'^L|(\cos\phi_2'^L + j\sin\phi_2'^L) \quad (27)$$

where $S_R=1/k_R$ and $S_L=1/k_L$. Additionally, the following formula (28) is established in relation to the origin correction vectors:

[Formula 19]

$$r_{10}{}^R = r_1{}^R - r_1'^R = |r_1{}^R|(\cos\phi_{r_1}{}^R + j\sin\phi_{r_1}{}^R) - s_R|\theta_1{}^R|(\cos\phi_1{}^R + j\sin\phi_1{}^R)$$

$$r_{20}{}^R = r_2{}^R - r_2'^R = |r_2{}^R|(\cos\phi_{r_2}{}^R + j\sin\phi_{r_2}{}^R) - s_R|\theta_2{}^R|(\cos\phi_2{}^R + j\sin\phi_2{}^R)$$

$$r_{10}{}^L = r_1{}^L - r_1'^L = |r_1{}^L|(\cos\phi_{r_1}{}^L + j\sin\phi_{r_1}{}^L) - s_L|\theta_1{}^L|(\cos\phi_1{}^L + j\sin\phi_1{}^L)$$

$$r_{20}{}^L = r_2{}^L - r_2'^L = |r_2{}^L|(\cos\phi_{r_2}{}^L + j\sin\phi_{r_2}{}^L) - s_L|\theta_2{}^L|(\cos\phi_2{}^L + j\sin\phi_2{}^L) \quad (28)$$

In the eight relational expressions that take into account the real number components and imaginary number components of the formula (28), there are a total of eight unknown parameters: four components of the two origin correction vectors $r_0{}^R$, $r_0{}^L$, the parameters $S_R$, $S_L$, which are reciprocal numbers of the gain value k, and the two-dimensional coordinates of the point of gaze Q. The image processor 7, therefore, can calculate the eight parameters based on the camera images captured by at least the two cameras and determine the calculated parameters as the correction values. The image processor 7 may use a function having a non-linear relationship between the vector $|r_i'|$ and the angle $\theta_i$, in which case, even when the number of unknown parameters is increased by two, the unknown parameters can be corrected with three cameras by using relational expressions similar to the formulae (15) to (17).

Also, CCD cameras, CMOS cameras or other digital cameras may be used as the cameras 2a, 2b, 2c, 2d.

In the present invention according to the aspect described above, the line of sight direction calculation step can calculate the angle $\theta$ using the following formula (2) that includes the coefficient k and the vector $r_0$ as the undetermined constants, and the undetermined constant determination step can determine the coefficient k and the vector $r_0$:

$$\theta = k|r - r_0| \quad (2)$$

In this case, the function f and the origin correction are determined, and therefore the coefficient k can be obtained accurately. Consequently, the angle $\theta$ of line of sight can be calculated more accurately throughout the entire screen where the viewpoints of the subject are detected.

The line of sight direction calculation step can also calculate the inclination $\phi$ of the vector r that is corrected based on the vector $r_0$ on the face images captured by the N number of cameras. The undetermined constant determination step can calculate the M number of undetermined constants by using a plurality of relational expressions derived based at least on the inclination $\phi$ and the angle $\theta$. In this case, because the function f is corrected based on the angle of line of sight along the image surface captured by each camera, the corrected line of sight direction can always be calculated accurately, and gaze calculation calibration can be realized while reducing the number of cameras.

The line of sight direction calculation step can calculate the angles $\theta$ corresponding to the N number of cameras when the subject is caused to gaze at a specified point on a predetermined surface. The undetermined constant determination step can calculate the M number of undetermined constants based on the position of the specified point and the angle $\theta$. The M number of undetermined constants can be determined by causing the subject to gaze at one specified point on a predetermined screen, resulting in a reduction of the burden on the subject and immediate execution of gaze point detection, the burden being imposed at the time of the calibration process.

The vector calculation step can calculate the vectors $r_R$, $r_L$ between the corneal reflection point and the pupil of each of the left and right eyes of the subject based on the face image captured by each of the N number of cameras. Based on the vectors $r_R$, $r_L$ corresponding to the N number of cameras, the line of sight direction calculation step can calculate the angles $\theta_R$, $\theta_L$ of lines of sight of the right and left eyes of the subject with respect to the base line of each of the N number of cameras by using the function f. The undetermined constant determination step can determine the M number of undetermined constants by using a condition that an intersection points of a predetermined plane with lines of sight of the right and left eyes coincide with each other, based on the angles $\theta_R$, $\theta_L$ corresponding to the N number of cameras. According to this configuration, the function f can be corrected automatically without causing the subject to gaze at a specified point, further reducing the burden that is imposed on the subject at the time of the calibration process.

INDUSTRIAL APPLICABILITY

The present invention is intended to be used as a method and a device for detecting a point of gaze of a subject on a predetermined plane on the basis of an image of the subject, and is capable of realizing high-speed and highly accurate gaze point detection while reducing the burden imposed on the subject.

REFERENCE SIGNS LIST

1 ... Gaze point detection device, 2a, 2b, 2c, 2d ... Camera, 3a, 3b, 3c, 3d ... Light source, 4 ... Light-emitting circuit (control circuit), 5 ... Synchronizing signal generator (control circuit), 6 ... Delay circuit (control circuit), 7 ... Image processor (image processing unit), 8 ... Display device, 9a, 9b, 9c, 9d ... Aperture, A ... Subject, G ... Corneal reflection point, P ... Center of pupil, Q ... Point of gaze, r, $r_1$, $r_2$ ... Vector, $r_0$, $r_{10}$, $r_{20}$ ... Origin correction vector

The invention claimed is:
1. A gaze point detection method, comprising:
a face image generation step of generating face images of a subject by using an N number of cameras (wherein N is a natural number of 2 or more) and a plurality of light sources;
a vector calculation step of calculating vectors r based on the face images generated by the N number of cameras, the vectors r each representing an actual distance between a center of a pupil of the subject and a corneal reflection point on a cornea of the subject on which light from the light sources reflects;

a line of sight direction calculation step of calculating angles θ of a gaze of the subject with respect to base lines connecting the center of the pupil and the N number of cameras, based on the vectors r corresponding to the N number of cameras, by using the following formula (1) in use of a function f and an M number of undetermined constants (wherein M is a natural number of 3 or more) including at least an offset vector $r_0$ of each of the vectors r;

$$\theta = f(|r-r_0|) \qquad (1)$$

an undetermined constant determination step of determining the M number of undetermined constants included in the function f, by using a plurality of relational expressions that are derived based at least on the angles θ calculated with respect to the N number of cameras;

wherein the line of sight direction calculation step calculates the angles θ using the following formula (2) that includes a coefficient k and the vector $r_0$ as the undetermined constants;

$$\theta = k|r-r_0| \qquad (2), \text{ and}$$

the undetermined constant determination step determines the coefficient k and the vector $r_0$; and a gaze point detection step of detecting a point of gaze of the subject on the basis of the line of sight direction calculated in the line of sight direction calculation step, by using the M number of undetermined constants determined in the undetermined constant determination step, wherein the number N of cameras is set at M×½ or higher;

the vector calculation step calculates vectors r corresponding to at least three cameras among the N number of cameras when the subject is caused to gaze at one specified point on a predetermined plane, the undetermined constant determination step derives three relational expressions each including the coefficient k and the vector $r_0$, by applying the vectors r calculated by the vector calculation step, and the angles θ calculated corresponding to at least three cameras, to the formula (2), and determines the coefficient k and the vector $r_0$ by establishing simultaneous equations with the three relational expressions.

2. The gaze point detection method according to claim 1, wherein the line of sight direction calculation step calculates an inclination φ of the vector r on the face images captured by the N number of cameras, the inclination φ being obtained after correcting the vector r based on the vector $r_0$, and the undetermined constant determination step determines the M number of undetermined constants by using a plurality of relational expressions derived based at least on the inclination φ and the angles θ.

3. The gaze point detection method according to claim 1, wherein the vector calculation step calculates vectors $r_R$, $r_L$, respectively, from corneal reflection points of right and left eyes of the subject to the centers of the pupils, based on the face images captured by the N number of cameras, the line of sight direction calculation step calculates angles $\theta_R$, $\theta_L$ of lines of sight of the right and left eyes of the subject with respect to the base lines associated with the N number of cameras, by using the function f, based on the vectors $r_R$, $r_L$ corresponding to the N number of cameras, and the undetermined constant determination step determines the M number of undetermined constants by using a condition that an intersection points of a predetermined plane with lines of sight of the right and left eyes coincide with each other, based on the angles $\theta_R$, $\theta_L$ corresponding to the N number of cameras.

4. A gaze point detection device for detecting a point of gaze of a subject based on face images of the subject, the device comprising:

an N number of cameras for acquiring the face images of the subject;

a plurality of light sources;

a control circuit for controlling the cameras and the light sources; and an image processing unit that includes a computer configured to process image signals output from the N number of cameras, wherein the image processing unit:

calculates vectors r based on the face images generated by the N number of cameras, the vectors r each representing an actual distance between a center of a pupil of the subject and a corneal reflection point on a cornea of the subject on which light from the light sources reflects;

calculates angles θ of a line of sight of the subject with respect to base lines connecting the center of the pupil and the N number of cameras, based on the vectors r corresponding to the N number of cameras, by using the following formula (1) in use of a function f and an M number of undetermined constants (wherein M is a natural number of 3 or more) including at least an offset vector $r_0$ of each of the vectors r;

$$\theta = f(|r-r_0|) \qquad (1)$$

determines the M number of undetermined constants included in the function f, by using a plurality of relational expressions that are derived based at least on the angles θ calculated with respect to the N number of cameras;

wherein the line of sight angle calculation step calculates the angles θ using the following formula (2) that includes a coefficient k and the vector $r_0$ as the undetermined constants;

$$\theta = k|r-r_0| \qquad (2), \text{ and}$$

the undetermined constant determination step determines the coefficient k and the vector $r_0$;

detects a point of gaze of the subject on the basis of the line of sight direction calculated using the formula (1) by using the M number of undetermined constants; and sets the number N of cameras at M×½ or higher;

the vector calculation step calculates vectors r corresponding to at least three cameras among the N numbers of cameras when the subject is caused to gaze at one specified point on a predetermined plane, the undetermined constant determination step derives three relational expressions each including the coefficient k and the vector $r_0$, by applying the vectors r calculated by the vector calculation step, and the angles θ calculated corresponding to at least three cameras, to the formula (2), and determines the coefficient k and the vector $r_0$ by establishing simultaneous equations with the three relational expressions.

* * * * *